United States Patent
Scheffler

(10) Patent No.: US 7,959,777 B2
(45) Date of Patent: *Jun. 14, 2011

(54) DEVICES, SYSTEMS AND METHODS FOR TESTING GAS SENSORS AND CORRECTING GAS SENSOR OUTPUT

(75) Inventor: Towner B. Scheffler, Butler, PA (US)

(73) Assignee: Mine Safety Appliances Company, Cranberry Township, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/215,295

(22) Filed: Jun. 26, 2008

(65) Prior Publication Data

US 2008/0302673 A1    Dec. 11, 2008

Related U.S. Application Data

(63) Continuation of application No. 10/839,455, filed on May 5, 2004, now Pat. No. 7,413,645.

(51) Int. Cl.
*G01N 27/26* (2006.01)
(52) U.S. Cl. ........................ 204/406; 73/23.21
(58) Field of Classification Search .................. 205/775; 73/1.07, 23.21; 204/401, 406, 414, 431
See application file for complete search history.

(56) References Cited

U.S. PATENT DOCUMENTS

| 5,202,637 | A | * | 4/1993 | Jones | 324/425 |
| 5,273,640 | A | * | 12/1993 | Kusanagi et al. | 204/401 |
| 5,667,653 | A | * | 9/1997 | Schneider et al. | 204/431 |

FOREIGN PATENT DOCUMENTS

| EP | 0269794 A2 * | 9/1987 |
| EP | 0990895 A2 * | 5/2000 |
| EP | 1039293 A1 * | 9/2000 |
| WO | WO 03/016893 A2 * | 2/2003 |

* cited by examiner

*Primary Examiner* — Ula C Ruddock
*Assistant Examiner* — J. Christopher Ball
(74) *Attorney, Agent, or Firm* — Henry E. Bartony, Jr.; James G. Uber

(57) ABSTRACT

A method of adjusting the output of an electrochemical sensor including a working electrode and a counter electrode, includes: electronically causing a current flow between the working electrode and the counter electrode via an electrolyte without introducing a test analyte to the electrochemical sensor; measuring a response of the sensor to the current demand resulting from the electronically generated current flow; and using the measured response to adjust the sensor output during sampling of an analyte gas.

19 Claims, 14 Drawing Sheets

DEVICES, SYSTEMS AND METHODS FOR TESTING GAS SENSORS AND CORRECTING GAS SENSOR OUTPUT

CROSS-REFERENCE TO RELATED APPLICATION

This application is a continuation of U.S. patent application Ser. No. 10/839,455, the disclosure of which is incorporated herein by reference.

FIELD OF THE INVENTION

The present invention relates generally to devices, systems and methods for testing gas sensors, and, more particularly, to devices, systems and methods for testing gas sensors electronically and correcting the output of the gas sensor on the basis of the electronic test.

BACKGROUND OF THE INVENTION

Amperometric or fuel cell-type gas sensors typically include at least two electrocatalytic electrodes (an anode and a cathode), at least one of which is a gas diffusion electrode or working electrode. The working electrode can be either the anode or the cathode in any given sensor. The gas diffusion electrode typically includes fine particles of an electrocatalytic material adhered to one side of a porous or gas-permeable membrane. The gas sensor can also include a third, reference electrode to maintain the working electrode at a known voltage or potential.

The electrocatalytic side of the working electrode is in ionic contact with the second electrode (the counter electrode, whether the anode or the cathode) via an electrolyte (for example, a liquid electrolyte, a solid electrolyte or a quasi-solid state electrolyte). A liquid electrolyte is typically a solution of a strong electrolyte salt dissolved in a suitable solvent, such as water. Quasi-solid state electrolytes can, for example, include a liquid electrolyte immobilized by a high-surface-area, high-pore-volume solid. The working electrode and the counter electrode are also in electrical contact via an external circuit used to measure the current that flows through the sensor.

Various manufacturers of gas detectors include some means of monitoring the presence of an electrochemical gas sensor and determining its serviceability. One common method is to generate a suitable target gas (either the analyte of interest or a suitable stimulant) and monitor the response of the sensor to that generated gas. As typical gas generators are electrochemical cells themselves, there is a correlation between the amount of current used to produce the gas sample and the concentration of that sample. The method yields the presence of a working gas sensor and can be used to correct the output of the sensor. However, the technique has several disadvantages including, for example, complexity and ambiguity. In that regard, the gas generation cell is subject to the same forces of degradation to which the sensor is subject. Moreover, unless some method of monitoring the condition of the gas generator is employed, these methods can result in a self-consistent, but analytically incorrect indication of sensor health.

U.S. Pat. No. 6,370,940 describes a method for determining the concentration of a gas sample that could be used to actually calibrate the sensor if the concentration of the gas were known. The method requires a known concentration of test gas and the means to modulate the flow of the gas to the sensor.

In a number of current sensors, the presence of a sensor and sensor serviceability is determined via electronic testing. Calibration of such sensors requires measurement of sensor response during exposure to a standard calibration gas having a known concentration of analyte gas. For example, U.S. Pat. No. 6,428,684 discloses a method of determining the response of a sensor and comparing the determined sensor response with a "normal" response. The testing purportedly determines abnormalities in sensor operation and predicts future failure. In one embodiment, a potentiostat circuit is modified to allow the sensor to be tested galvanostatically. A small current flowing through the sensor for short time periods allows the electrode capacitance to be determined. Passing larger currents through the sensor, and especially by varying the current passed with time, provides a means to characterize the electrochemical properties of the sensor. Comparison of these electrical properties with reference values or with data obtained at a different time is used to determine the functional status of the sensor.

U.S. Pat. No. 6,049,283 describes a method of detecting the presence of a serviceable electrochemical gas sensor by measuring the electronic noise in the output of the sensor amplifier.

U.S. Pat. No. 6,629,444 describes a method of diagnosing defects in electrochemical gas sensors by suddenly changing the water vapor pressure of the air surrounding the sensor to more dry or more humid air thereby causing a sharp change in the acidity at the working electrode and hence a transient current in the sensor which can be used to monitor the sensor's condition.

U.S. Pat. No. 6,123,818 describes a method of detecting the presence of a serviceable electrochemical gas sensor by applying a transient to the non-inverting input of the operational amplifier that amplifies the output current of the sensor. The gain of that operational amplifier is monitored. If the gain resulting from the transient is high, a serviceable sensor is present; if the gain is low, a serviceable sensor is not present. U.S. Pat. No. 6,251,243 describes a similar method of detecting the presence of a serviceable gas sensor. Under this method, the transfer function of the operational amplifier is monitored.

U.S. Pat. No. 5,202,637 describes a method for detecting the presence of an electrochemical gas sensor by applying a potential pulse or a periodically varying potential to the sensor. The output current of the sensor is monitored. If a current is detected in response to the potential signal, then a sensor is present.

From this it is clear that it is desirable to develop improved devices, systems and methods for testing gas sensors and, preferably, devices, systems and methods suitable to correct the output of the gas sensor on the basis of an electronic test.

SUMMARY OF THE INVENTION

In one aspect, the present invention provides a method of adjusting the output of an electrochemical sensor having at least a working electrode, a counter electrode and an electrolyte. The electrochemical sensor can also include a reference electrode as known in the art. The method includes the steps of: electronically causing a current flow between the working electrode and the counter electrode; measuring a response of the sensor to the current demand; and using the measured response to adjust (preferably automatically) the sensor output during sampling of an analyte gas. The step of using the measured response to adjust (preferably automatically) the sensor output can, for example, include the step of applying an algorithm to the measured output of the sensor. The algorithm can be hardwired in circuitry or stored in a computer memory.

In one embodiment, a constant current is caused to flow between the working electrode and the counter electrode and the measured response is a potential difference. In another embodiment, a constant potential difference is maintained between the working electrode and the counter electrode and the measured response is current.

The electrolyte, which provides ionic conductivity between the working electrode and the counter electrode, can be an aqueous electrolyte or an organic electrolyte. The electrolyte can also be a liquid electrolyte, a quasi-solid electrolyte or a solid electrolyte. In general, quasi-solid electrolytes include a liquid ionic conductor immobilized by a high-surface-area, high-pore-volume solid. In general, solid electrolytes are solid ionic conductors such as a NAFION® membrane (a perfluorosulfonate ionomer), available from E.I. DuPont de Nemours & Co.

In another aspect, the present invention provided a sensor including a working electrode; a counter electrode; an electrolyte; a power source in electrical connection with the working electrode and the counter electrode to electronically cause a current flow between the working electrode and the counter electrode; circuitry to measure a response of the sensor to the electronically generated current flow; and an output system which adjusts the output of the sensor as a function of the measured response of the sensor to the electronically generated current flow.

In still a further aspect, the present invention provides a method of adjusting the output of an electrochemical sensor, including the steps of: simulating the presence of an analyte gas electronically; measuring a response of the sensor to the electronic simulation; and adjusting the output of the sensor as a function of the measured response to the electronic simulation.

The method of testing or interrogation of a sensor and subsequent correction of sensor output of the present invention provides a real-time measure of sensor performance. The electronic interrogation exercises or effects the sensor in generally the same way that exposure to target gas does. That is, the test method of the present invention measures the ability of the sensor to respond to or comply with a current demand between the working electrode and the counter electrode. The appearance of target gas at the working electrode results in a demand for a current to flow, internally, through the sensor. This flow of current involves faradaic movement of electrons across the phase boundary regions of the working electrode and the counter electrode and ionic current flow through the electrolyte of the sensor. The test method of the present invention causes current to flow through the sensor in the same manner. However, the magnitude of the current demand imposed by the interrogation method of the present invention is fixed as a function of the electronic components through which it is imposed. Therefore, the response function of the sensor varies only as a function of age, environmental exposure, or other internal variables of the sensor.

DETAILED DESCRIPTION OF THE INVENTION

Figure 1:
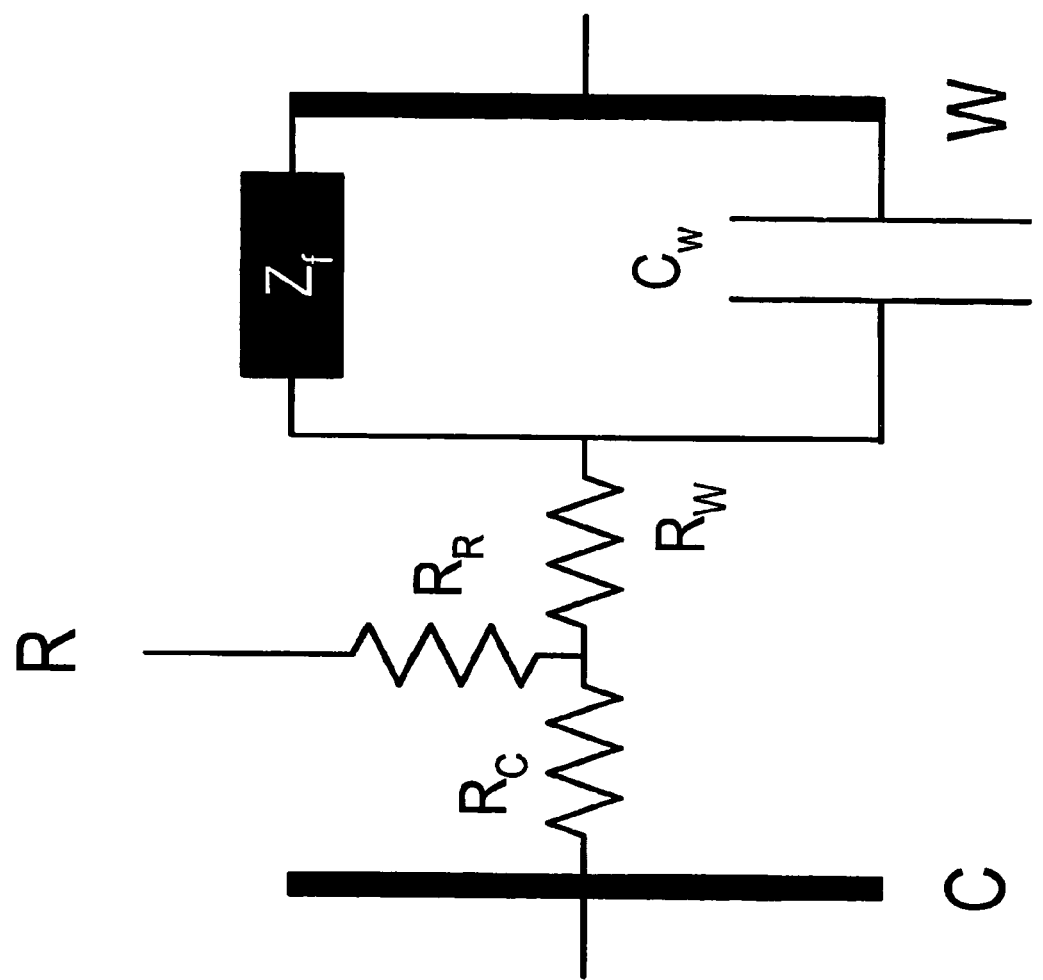
FIG. 1 illustrates an equivalent circuit used to describe electrochemical cells.

As a result of its structure, a fuel cell-type electrode can be modeled by reference to common analog electronic components, such as resistors and capacitors. An equivalent circuit that is commonly used to describe the behavior of electrochemical cells is shown in FIG. 1. See, for example, P. T. Kissinger and W. R. Heineman, eds., *Laboratory Techniques in Electroanalytical Chemistry*, New York: Marcel Dekker, Inc. (1984) and A. J. Bard and L. R. Faulkner, *Electrochemical Methods: Fundamentals and Applications*, New York: John Wiley and Sons (1980).

As illustrated in FIG. 1, a sensor can be described as resistance and capacitance in series. The resistance $R_R$ resulting from the reference electrode of FIG. 1 is not part of the current path of the analytical signal of the sensor. The resistive portion of this circuit is primarily a result of the solution (ionic) resistance of the electrolyte interspersed between the working electrode ($R_W$) and the counter electrode ($R_C$). The capacitive portion ($C_W$) of the equivalent circuit is primarily a result of the micro solution environment found very close to the surfaces of the metallic particles that comprise the working electrode. As a result of electrostatic forces, the volume of solution very close to the electrode surface is a very highly ordered structure. This structure is important to understanding electrode processes. The volume of solution very close to the electrode surface is variously referred to as the diffusion layer, diffuse layer, and or the Helmholtz layer or plane.

The magnitudes of the resistance and capacitance present in an electrochemical cell are a result of the nature and identities of the materials used in its fabrication. The resistance of the electrolyte is a result of the number and types of ions dissolved in the solvent. The capacitance of the electrode is primarily a function of the effective surface area of the electrocatalyst. In an ideal world, these quantities are invariant. However, the solution resistance present in an amperometric gas sensor that utilizes an aqueous (water-based) electrolyte may change, for example, as a result of exposure to different ambient relative humidity levels. As water transpires from the sensor, the chemical concentration of the ionic electrolyte increases. This concentration change can lead to increases or decreases in the resistivity of the electrolyte, depending on the actual electrolyte used. Electronic parameters for several amperometric gas sensors are set forth below in Table 1.

TABLE 1

| Sensor Type | RMS noise, µA | AC impedance, Ω | Capacitance, F | Fundamental Frequency, Hz |
|---|---|---|---|---|
| CO | 0.689 | 4.48 | 0.3089 | 0.723 |
| $H_2S$ | 8.847 | 4.53 | 0.2472 | 0.893 |
| $NO_2$ | 0.480 | 16.99 | 1.464 | 0.040 |
| $Cl_2$ | 0.064 | 74.9 | 0.0379 | 0.352 |
| NO | 0.162 | 2.82 | $1.65 \times 10^{-2}$ | 21.5 |
| HCl | 0.124 | 2.72 | $1.32 \times 10^{-4}$ | 2785 |
| HCN | 0.057 | 252 | 0.0041 | 0.968 |
| $NH_3$ | 0.584 | 7.83 | 0.1805 | 0.708 |

Figure 2:
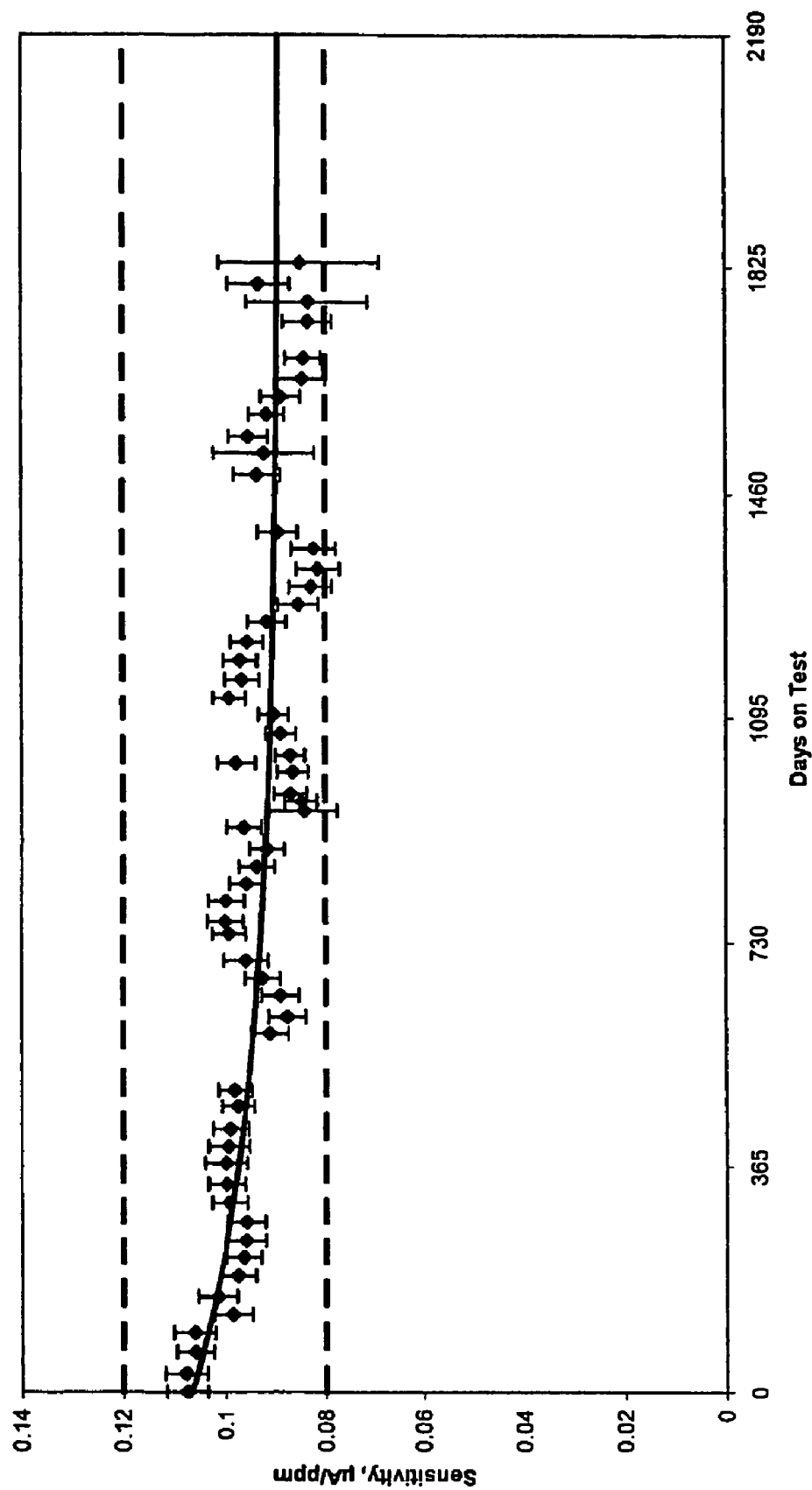
FIG. 2 illustrates long term test data for a group of amperometric carbon monoxide (CO) sensors.

Moreover, even for substances normally thought of as insoluble in a particular solvent, there is a small, but finite concentration of the substance in the solvent. For example, there is a very small, but finite concentration of metal from electrodes dissolved in the electrolyte of an electrochemical sensor. This small concentration of dissolved metal is constantly in flux. That is, metal atoms are constantly dissolving from the electrode and then replating somewhere else. The net effect of this process is to decrease the effective surface area of the electrode. This has the effect of lowering the sensor capacitance over time. Both of the above-described effects have the net effect of changing the sensitivity of the sensor over its lifetime. FIG. 2 depicts the accumulation of such aging effects over the life of representative amperometric carbon monoxide sensors.

The data set forth in FIG. 2 resulted from a long-term study of the behavior of representative carbon monoxide sensors, a common example of fuel cell-type sensors. The carbon monoxide sensors tested in FIG. 2 were Series 25 sensors available from Mine Safety Appliances Company. Such sensors were fabricated generally as described in U.S. Pat. No. 5,338,429, the disclosure of which is incorporated herein by reference. The electrodes were fabricated using a standard fabrication technique in which an electrochemically active powder is deposited upon a porous membrane. In that regard, the electrochemically active surfaces of both the working electrode and the counter electrode included a platinum electrocatalyst. The electrolyte used in the sensors was a liquid, aqueous, acidic electrolyte.

The data points of FIG. 2 were the mean sensitivity data observed for a group of forty (40) sensors. The error bars were the 99.99% confidence interval, calculated about the mean. The solid line was the result of a non-linear regression analysis of the mean data. The equation describing this line was of the form $y=a+b \cdot \log(-x/c)$, which is descriptive of a first order kinetic process as would be expected for the dissolution-replating model discussed above. See, for example, S. W. Benson, *The Foundations of Chemical Kinetics*. New York: McGraw-Hill (1960). The "wobble" in the mean data about the calculated line is believed to be a result of seasonal changes in the ambient relative humidity to which the test sensors were exposed during the experiment.

Figure 3:
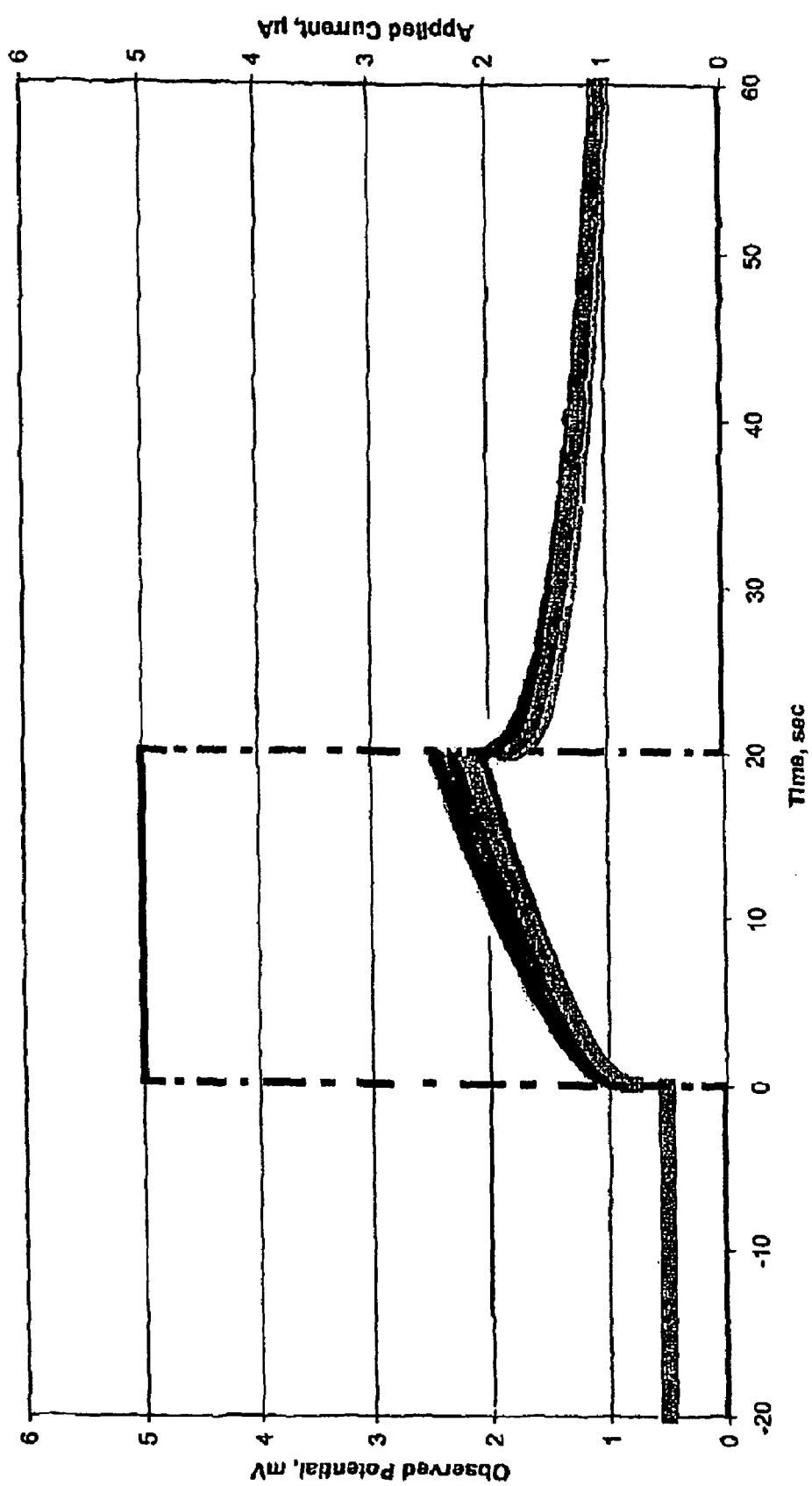
FIG. 3 illustrates electronic interrogation of amperometric carbon monoxide gas sensors.

FIG. 3 depicts the observed potential as a function of time for an electronic interrogation of an amperometric sensor under the method of the present invention. The heavy broken line, plotted against the right-hand abscissa, represents the current pulse used to interrogate a sensor. In this experiment, the pulse was 5 µA ($5 \times 10^{-6}$ A) in magnitude and lasted for 20 seconds. The other lines in FIG. 3 represent the responses of seven different amperometric carbon monoxide sensors. In this case, the sensors were operated in the galvanic mode, with a load resistor of 1000Ω placed in electrical connection between the working electrode and counter electrode of the sensors. The signal derived from current flowing in the sensor was the potential drop observed across this resistor.

Based on the discussions above, the response curves of the sensors in FIG. 3 have the shape expected for the charging curve of a capacitor, that is a typical "RC" curve. In one embodiment, the analytical signal used to determine the "health" of a sensor was the algebraic difference in the observed potential just prior to the application of the current pulse (time "0" in the Fig.) and at the end of the pulse (time "20" in FIG. 3). The magnitude of the potential difference observed as a function of the application of the current pulse is an indicator of the presence and the health of the sensor.

The magnitude and duration of the current pulse was chosen arbitrarily. Although, the limitations on the magnitude and duration of the current pulse have mostly to do with experimental convenience, the magnitude of the current pulse preferably corresponds to application of a reasonably expected amount of target gas. In the example shown in FIG. 3, the 5 µA current pulse was roughly equivalent, for the sensors of the studies, to exposure to 75 ppm carbon monoxide (CO).

As discussed above, sensor presence and health is determined by the shape of the sensor's RC charging curve, being measured by observing the difference in sensor output at the beginning and the end of the current pulse. If the sensor is absent, the observed potential is equal to that which would be expected based on the magnitudes of the current pulse and the sensor load resistor. In the present case, that would be 5 mV ($5 \times 10^{-3}$ V) (E=IR). For the sensors of the studies of FIG. 3, the mean signal resulting from the application of the current pulse was approximately 1.8±0.2 mV. The sensors of the studies were fabricated a relatively short period of time before the studies and were known to be well operating sensors. Sensors with greater age and/or degraded health, for any reason, would display potential responses intermediate between approximately 1.8 and 5 mV.

Figure 4:
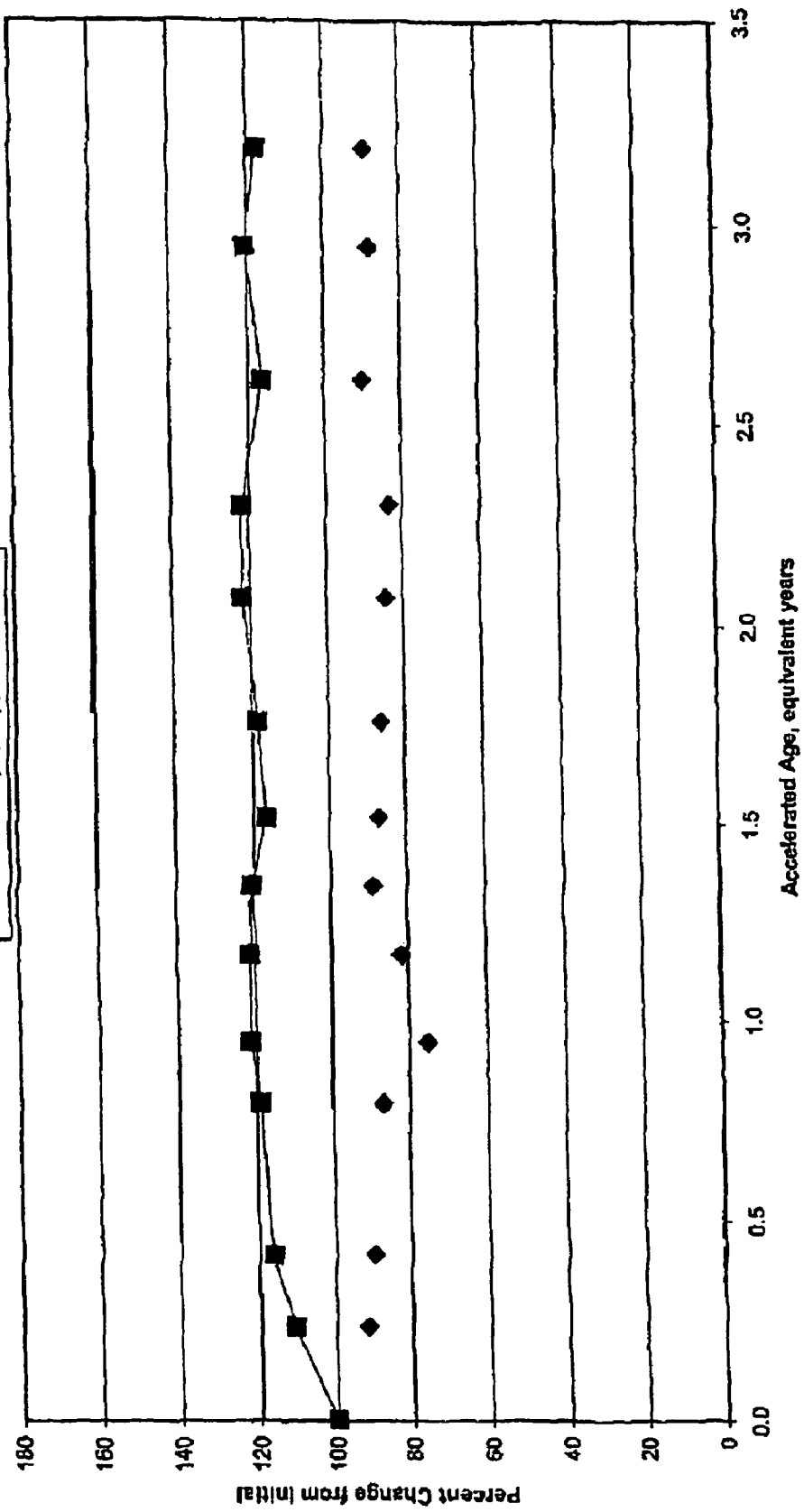
FIG. 4 illustrates the correlation between accelerated aging (sensitivity in µA/ppm) and the response function of electronic interrogation for carbon monoxide sensors.
Figure 5:
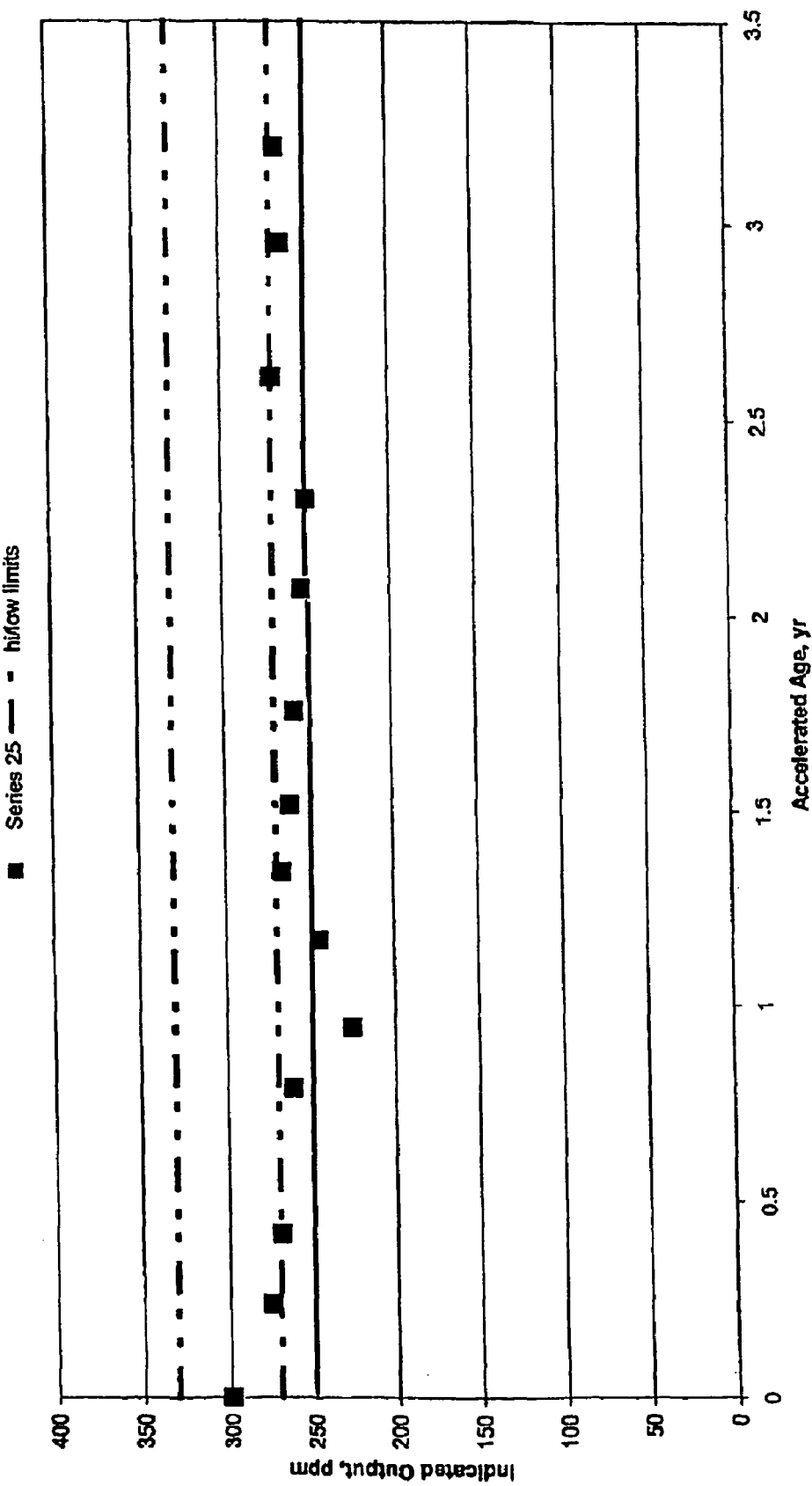
FIG. 5 illustrates uncorrected instrument performance for carbon monoxide sensors that underwent accelerated aging.
Figure 6:
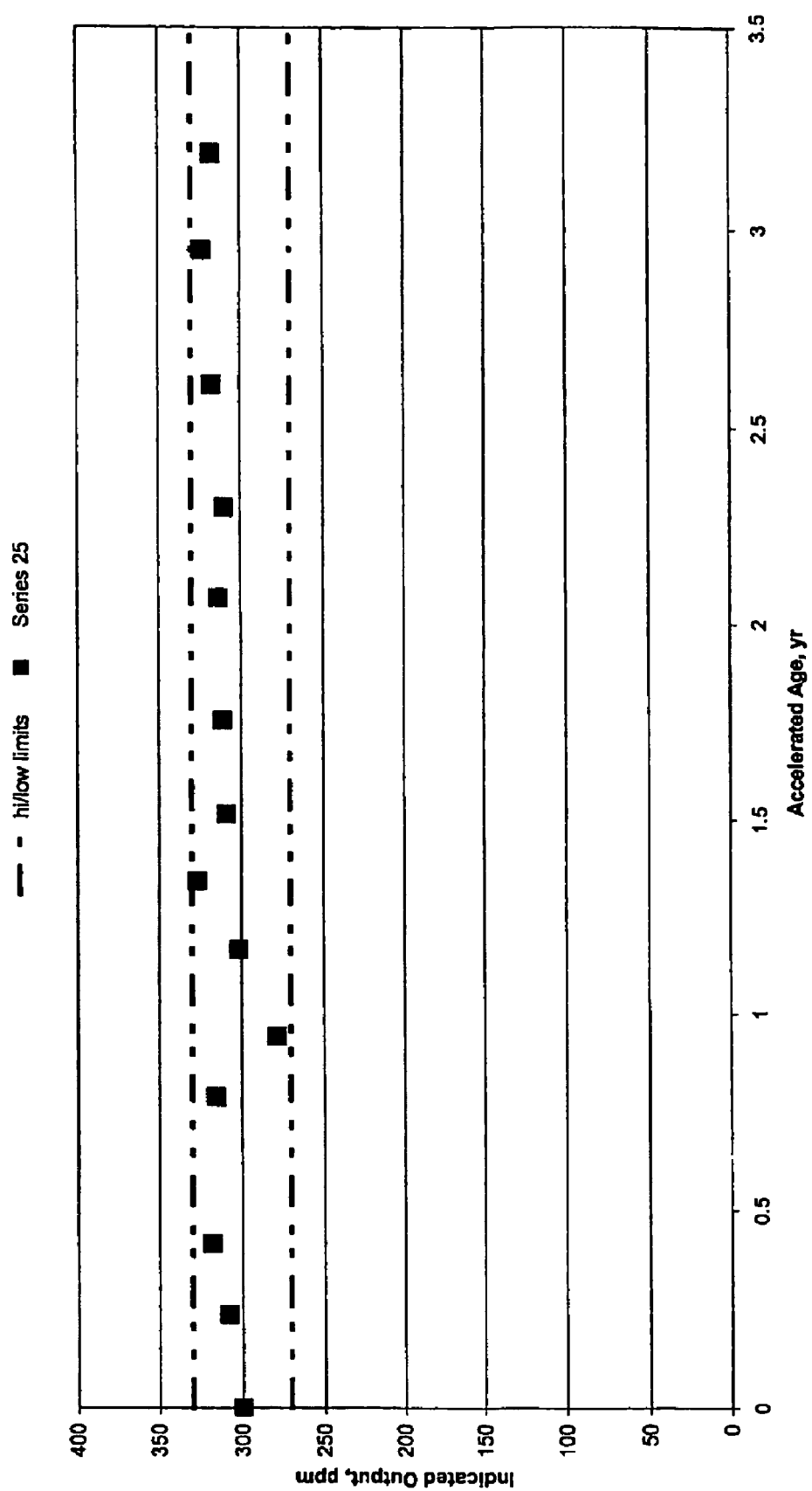
FIG. 6 illustrates corrected instrument performance for carbon monoxide sensors that underwent accelerated aging.

The present inventors have discovered that a sensor's response to an interrogative current pulse not only can be used to determine the sensor's presence and relative health, but can also be used to apply a real-time correction to the output signal of the sensor as the sensor ages or responds to a variety of environmental conditions. This correction of the output signal of a sensor is depicted in FIGS. 4, 5, and 6. FIG. 4 sets forth accelerated aging data for a set of twenty (20) carbon monoxide sensors. The data indicated by the filled diamonds (♦) in FIG. 4 was the change in the sensitivity (µA/ppm) of the sensors over the course of the experiment. The shape and magnitude of this change in sensitivity corresponds with the real-time aging data presented in FIG. 2. The sensors used in both experiments were of the same type and model. The data depicted by the filled squares (■) in FIG. 4 was the response (mV) to the electronic interrogation described above. As can be seen, the two data sets are essentially mirror images.

FIG. 5 sets forth the same data as FIG. 4; however, a scaling factor was applied to the data to simulate performance in an instrument. This simulation predicts the behavior of an uncorrected instrument over the course of the accelerated aging experiment. The experiment assumes that the instrument was calibrated at time zero to give the appropriate response for the application of 300 ppm CO. The broken lines in the Fig. represent the high-low accuracy and repeatability limits that are usually part of an instrument performance specification. In this case, a repeatability and accuracy of ±10 ppm of target level was assumed. Therefore the high and low limits correspond to 330 and 270 ppm CO indicated, respectively. The data in FIG. 5 indicate that, under the experimental test conditions, sensors age and fall out of specification within approximately 0.5 year, provided that the instrument was not recalibrated during this time.

FIG. 6 indicates the simulated behavior of an instrument using the response to electronic interrogation to correct the output of the sensor as it ages. The data represented in FIG. 4 as filled squares (■) was applied to the declining output of the sensors to bring the simulated instrument performance back into specification over the course of the experiment. The correction applied took the mathematical form:

$$S_C = \left(1 + \left(\frac{R_i - R_0}{R_0}\right)a\right)S_i$$

In the above equitation, $S_C$ was the corrected sensitivity of the sensor, $R_0$ and $S_0$ were the initial values of response function and sensitivity, respectively, $R_i$ and $S_i$ were the response function and sensitivity at any point in time during the experiment, and a was an adjustable parameter. The form of this equation is not unique; other correction functions may be used as well. The application of this correction factor to the experimental data brought the indicated response of the simulated instrument back into the specified range over the entire course of the experiment, thereby eliminating the need to recalibrate the sensor against a known standard calibration gas.

Figure 7:
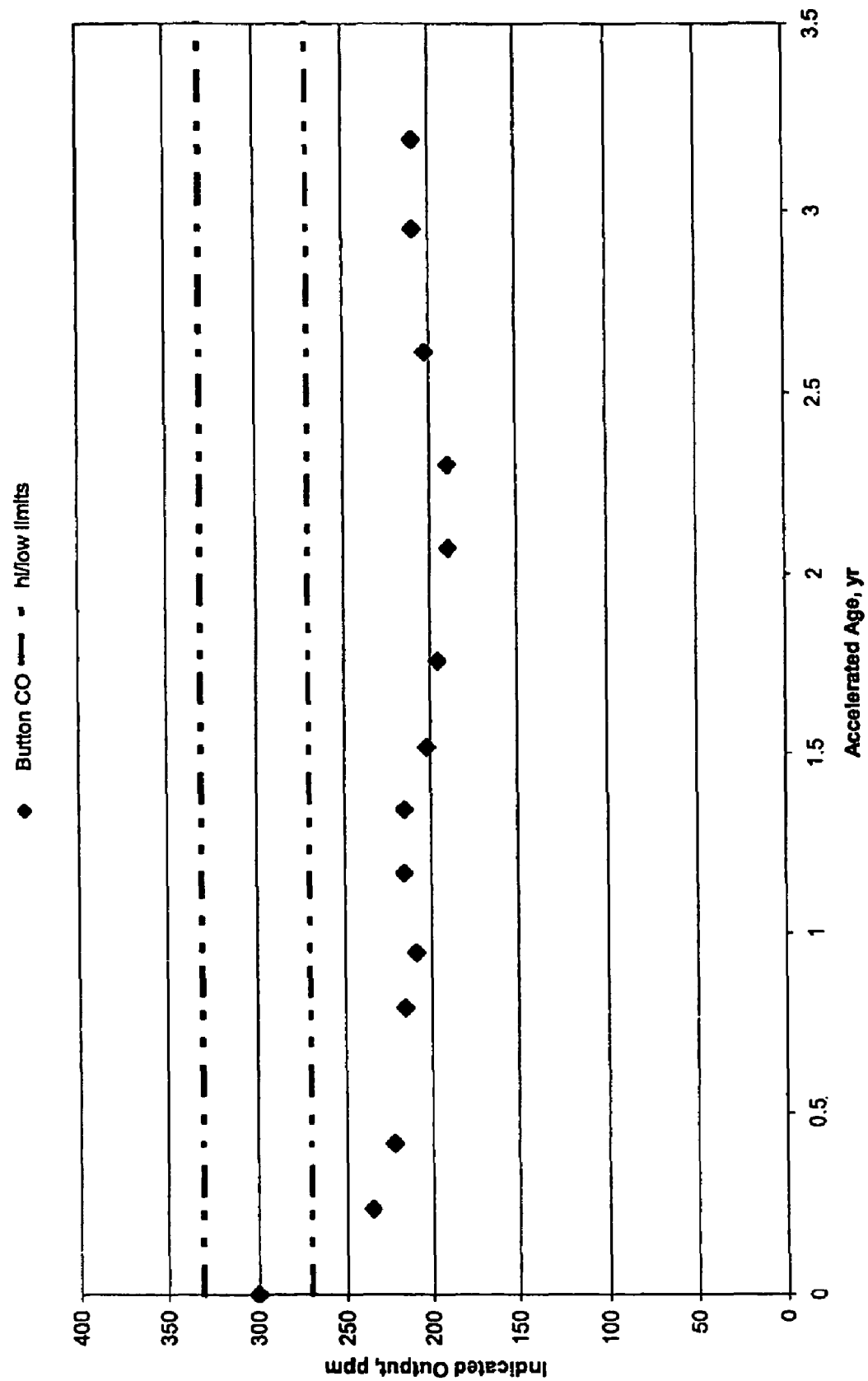
FIG. 7 illustrates uncorrected instrument performance for carbon monoxide BUTTON™ sensors that underwent accelerated aging.

FIG. 7 illustrates data similar to the data of FIG. 5 for carbon monoxide BUTTON™ sensors available from Mine Safety Appliances Company. Once again, the data predict the behavior of an uncorrected instrument over the course of the accelerated aging experiment. The data in FIG. 7 indicate that, under the experimental test conditions, sensors age and fall out of specification within approximately 0.25 year, provided that the instrument was not recalibrated during this time.

The BUTTON sensors used in the experiments of FIG. 7 are described in U.S. Pat. No. 5,667,653, the disclosure of which is incorporated herein by reference. The electrochemically active surfaces of both the working electrode and the counter electrode (fabricated using standard technique) included a platinum electrocatalyst. A quasi-solid state electrolyte was used in the carbon monoxide sensors of the present invention such as described, for example, in U.S. Pat. No. 5,667,653 and in U.S. patent application Ser. No. 10/164,539, filed Jun. 6, 2002 and assigned to the assignee of the present invention, the disclosure of which is incorporated herein by reference.

Figure 8:
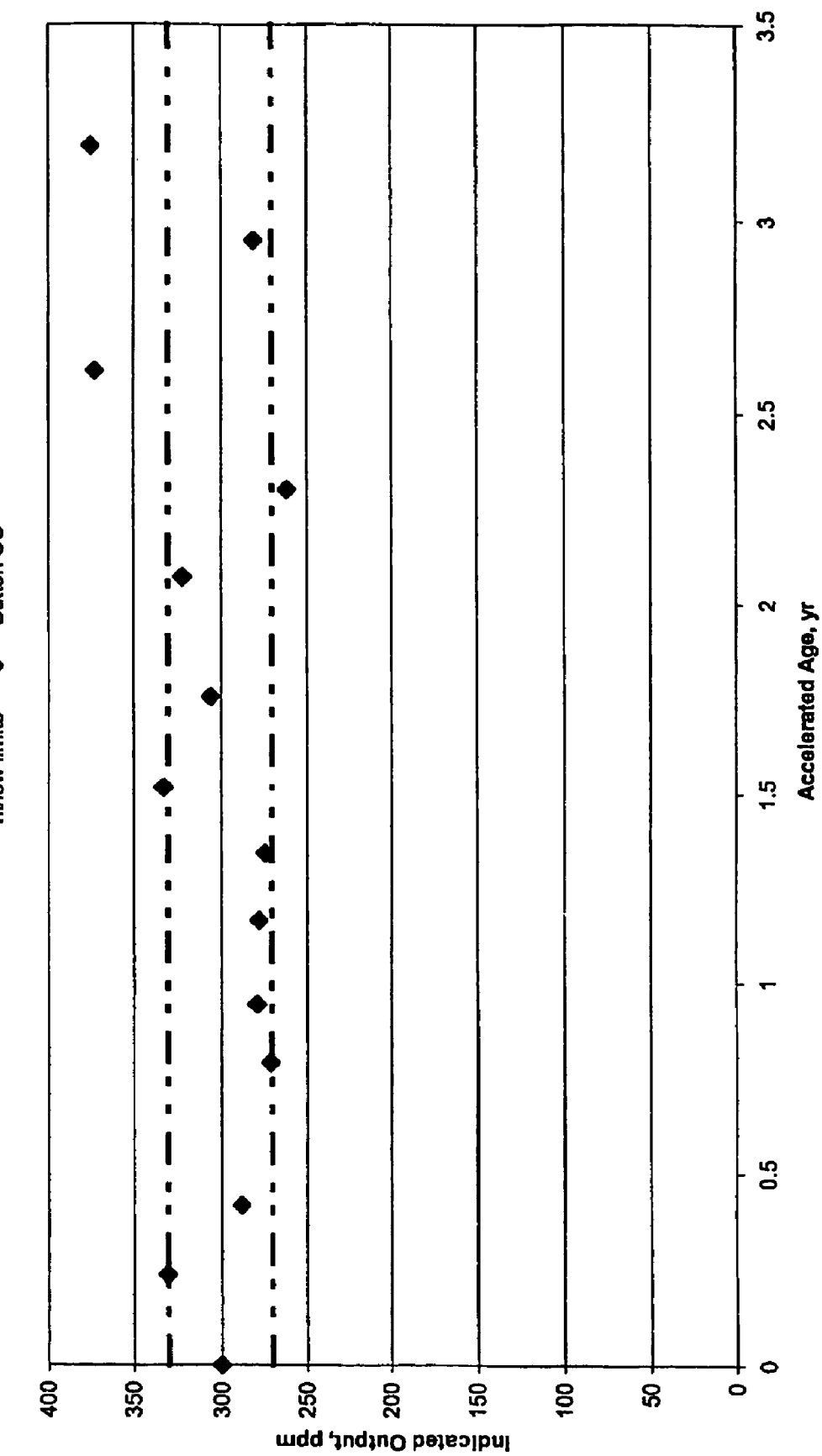
FIG. 8 illustrates corrected instrument performance for carbon monoxide BUTTON sensors that underwent accelerated aging.

FIG. 8 indicates the simulated behavior of an instrument using the response to electronic interrogation to correct the output of the sensor as it ages. The data represented in FIG. 8 as filled diamonds (♦) was applied to the output of the sensors to bring the simulated instrument performance substantially back into specification over the course of the experiment.

Figure 9:
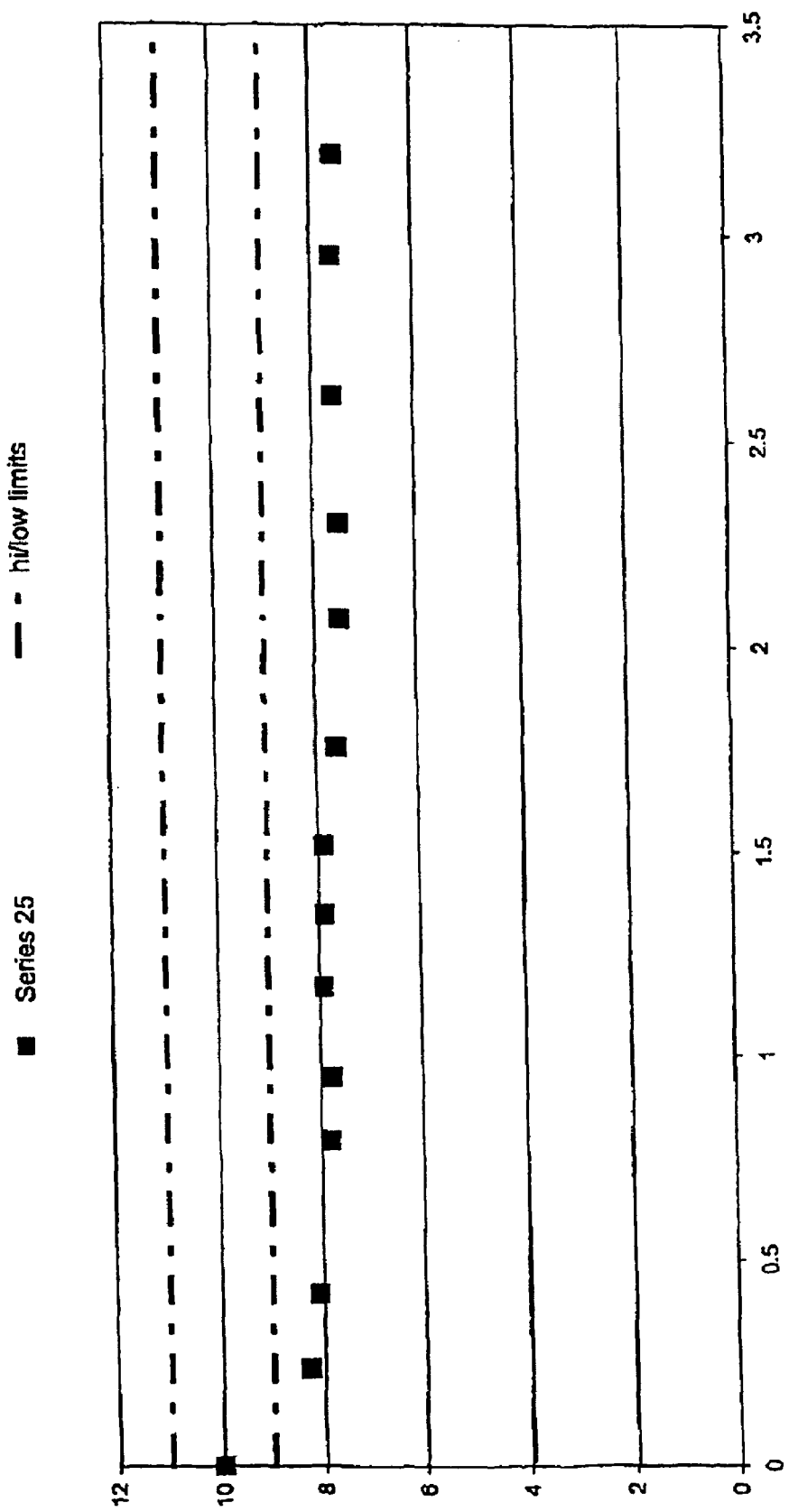
FIG. 9 illustrates uncorrected instrument performance for hydrogen sulfide sensors that underwent accelerated aging.

Several sets of experiments were also performed with hydrogen sulfide ($H_2S$) sensors. FIG. 9 sets forth accelerated aging data for a set of twenty (20) hydrogen sulfide sensors. The sensors were Series 25 sensors available from Mine Safety Appliances Company. The electrodes were fabricated using a standard fabrication technique in which an electrochemically active powder is deposited upon a porous membrane. In that regard, the electrochemically active surfaces of both the working electrode and the counter electrode included an iridium electrocatalyst. The electrolyte used in the sensors was a liquid, aqueous, acidic electrolyte.

The data indicated by the filled squares (■) in FIG. 9 was the change in the sensitivity (µA/ppm) of the sensors over the course of the experiment. A scaling factor was applied to the data to simulate performance in an instrument. As described above, the simulation predicts the behavior of an uncorrected instrument over the course of the accelerated aging experiment. The experiment assumed that the instrument was calibrated at time zero to give the appropriate response for the application of 10 ppm $H_2S$. The broken lines in the Fig. represent the high-low accuracy and repeatability limits that are usually part of an instrument performance specification. In this case, a repeatability and accuracy of ±1 ppm of target level was assumed. Therefore the high and low limits correspond to 9 and 11 ppm $H_2S$ indicated, respectively. The data in FIG. 9 indicate that, under the experimental test conditions, sensors age and fall out of specification within approximately 0.25 year, provided that the instrument was not recalibrated during this time.

Figure 10:
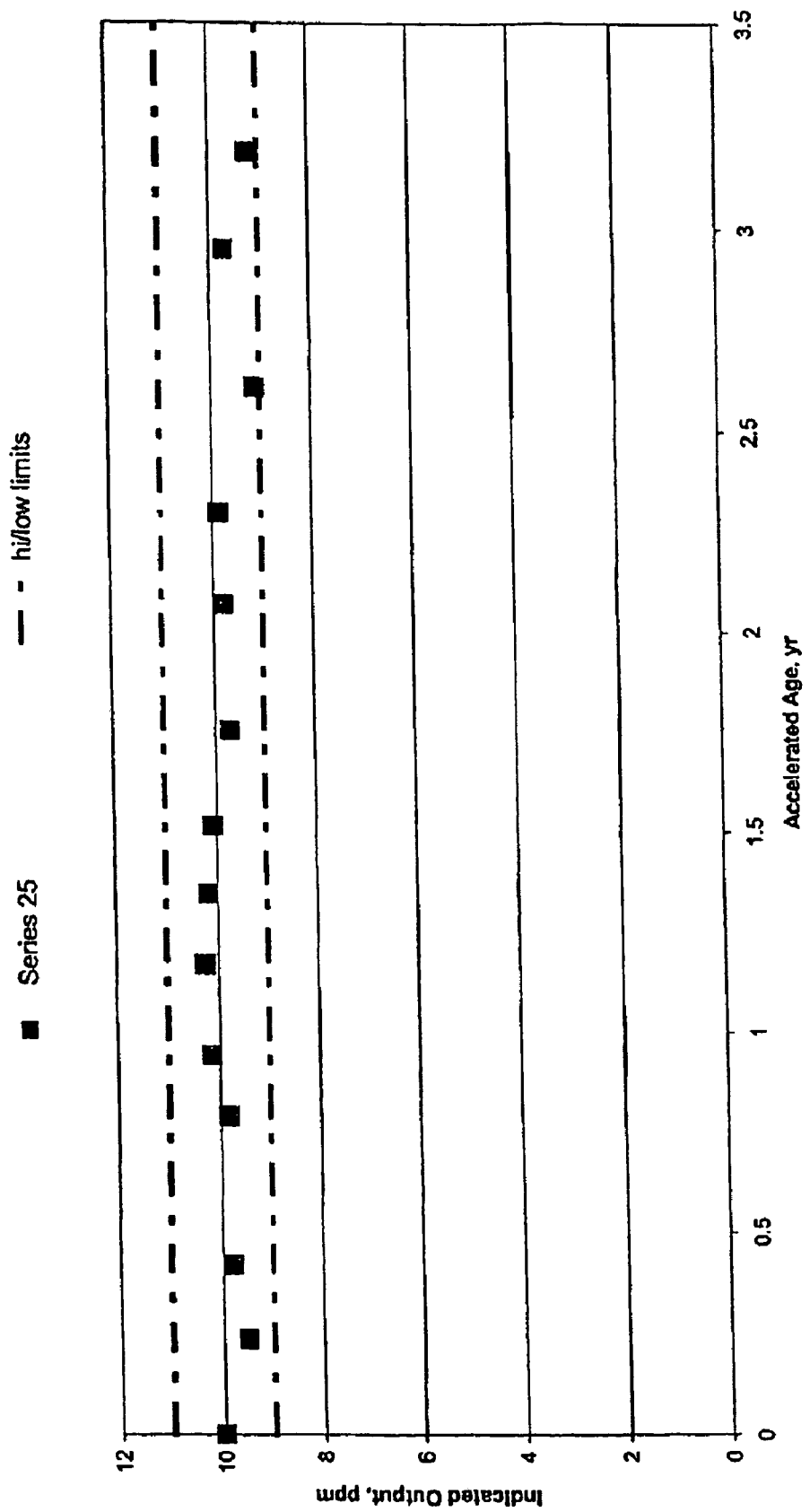
FIG. 10 illustrates corrected instrument performance for hydrogen sulfide sensors that underwent accelerated aging.

FIG. 10 indicates the simulated behavior of an instrument using the response to electronic interrogation to correct the output of the sensor as it ages. The data represented in FIG. 10 as filled squares (■) was applied to the output of the sensors to bring the simulated instrument performance back into specification over the course of the experiment.

Figure 11:
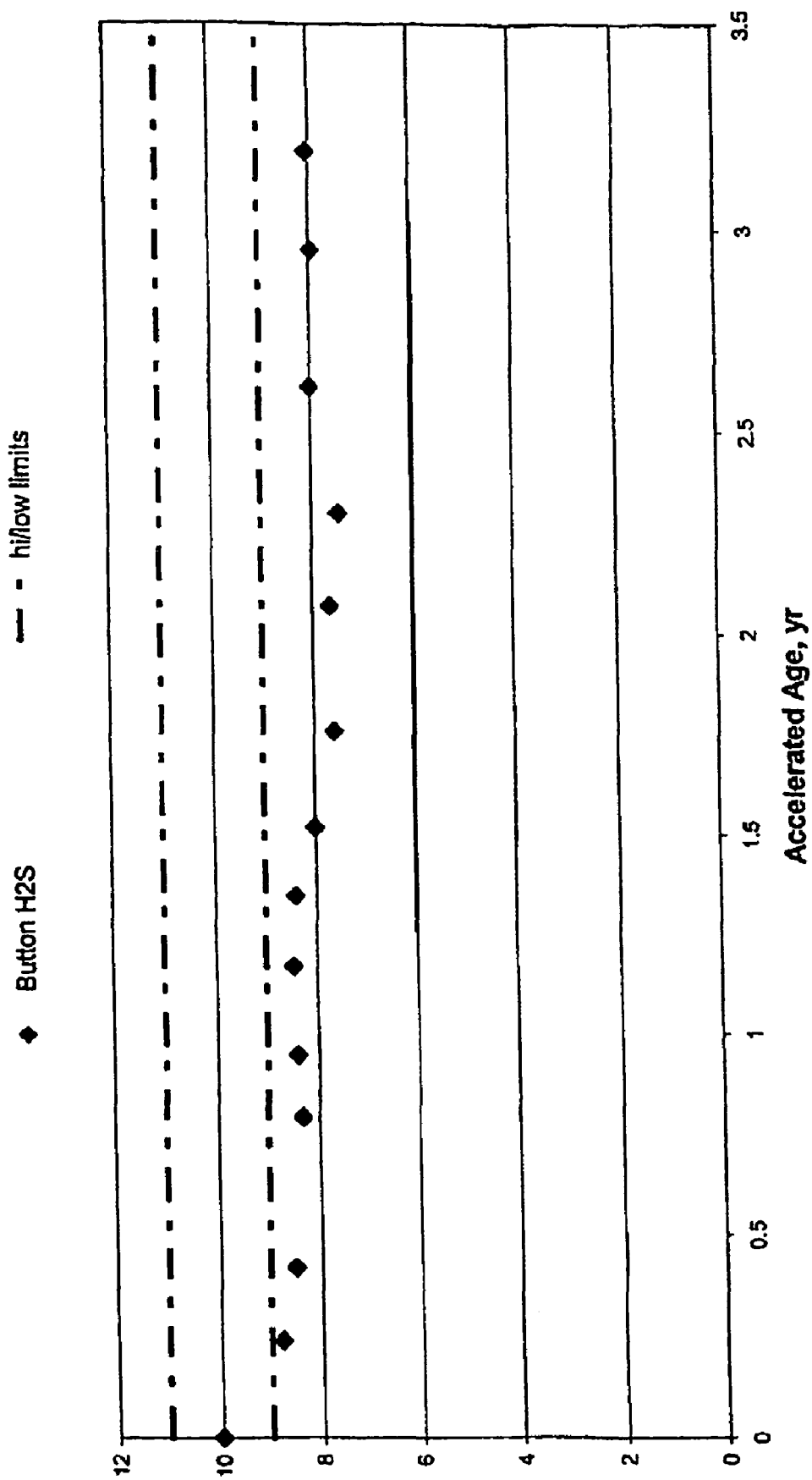
FIG. 11 illustrates uncorrected instrument performance for hydrogen sulfide BUTTON™ sensors that underwent accelerated aging.

FIG. 11 illustrates data similar to the data of FIG. 9 for hydrogen sulfide BUTTON™ sensors available from Mine Safety Appliances Company. Once again, the data predict the behavior of an uncorrected instrument over the course of the accelerated aging experiment. The data in FIG. 11 indicate that, under the experimental test conditions, sensors age and fall out of specification within approximately 0.25 year, provided that the instrument was not recalibrated during this time. The sensors of the experiments of FIG. 11 were fabricated generally as described in U.S. Pat. No. 5,667,653. However, the electrodes were bilayer electrodes fabricated as described in U.S. patent application Ser. No. 10/164,539. The electrochemically active surfaces of both the working electrode and the counter electrode included an iridium electrocatalyst. The electrolyte was a quasi-solid electrolyte as described above.

Figure 12:
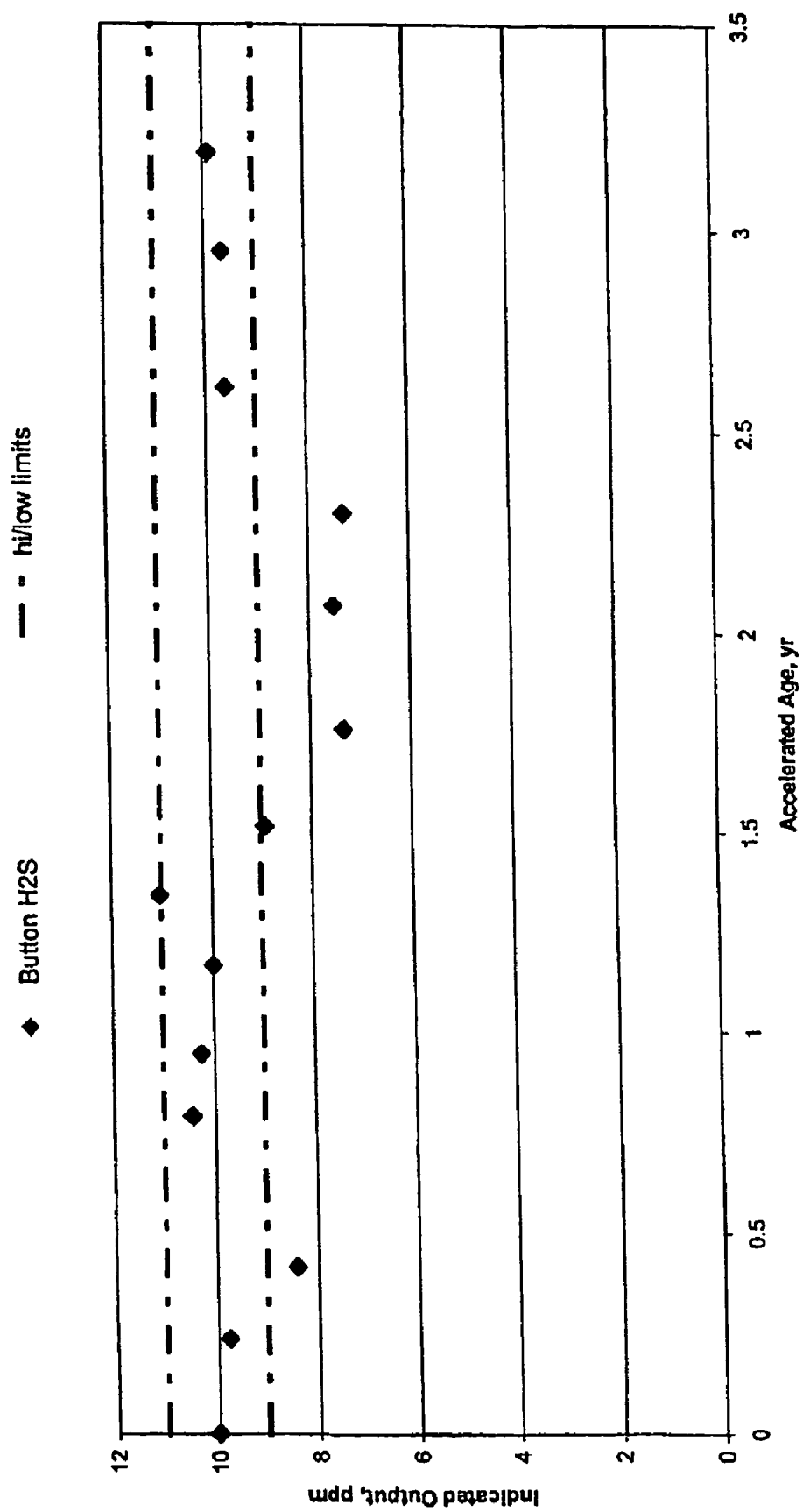
FIG. 12 illustrates corrected instrument performance for hydrogen sulfide BUTTON sensors that underwent accelerated aging.

FIG. 12 indicates the simulated behavior of an instrument using the response to electronic interrogation to correct the output of the sensor as it ages. The data represented in FIG. 12 as filled diamonds (♦) was applied to the output of the sensors to bring the simulated instrument performance substantially back into specification over the course of the experiment.

Figure 13A:
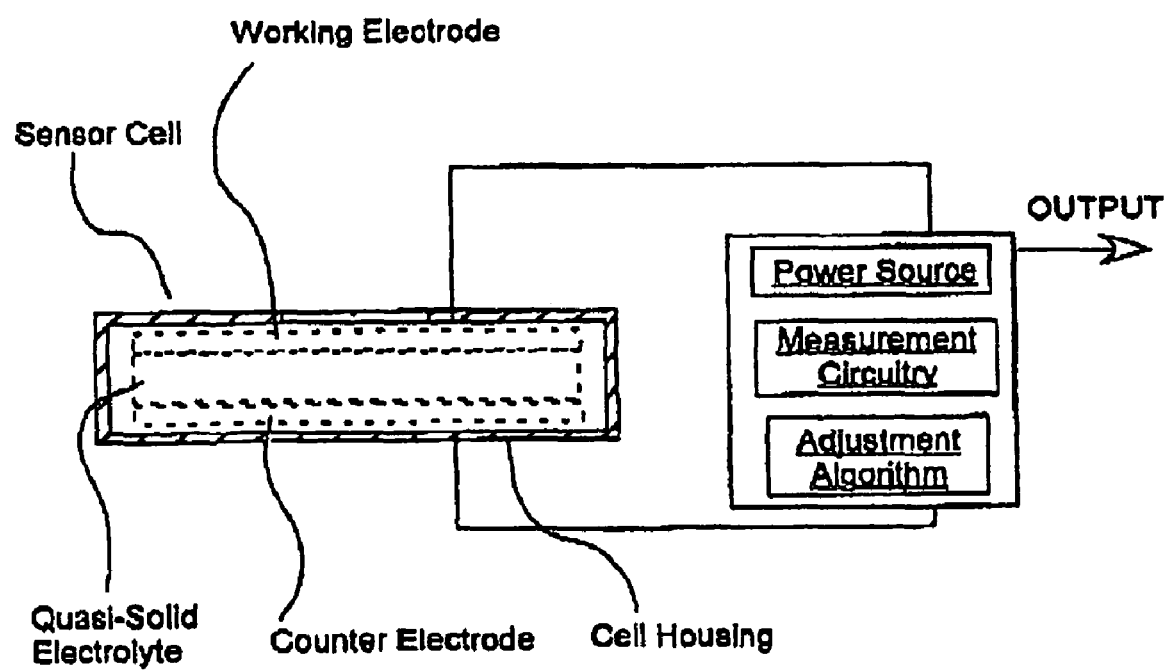
FIG. 13A illustrates a schematic representation of one embodiment of a sensor of the present invention.

FIG. 13A illustrates schematically a sensor of the present invention, wherein the cell housing of the sensor includes a working electrode and a counter electrode. A reference electrode (not shown) can also be provided as discussed above. An electrolyte such as a quasi-solid electrolyte provides ionic contact between the working electrode and the counter electrode. A power source is in electrical connection with the working electrode and the counter electrode to electronically cause a current flow between the working electrode and the counter electrode as described above. Circuitry measures the response of the sensor to the electronically generated current flow. An output system, which, for example, includes an algorithm as described above, adjusts the output of the sensor as a function of the measured response of the sensor to the electronically generated current flow.

Figure 13B:
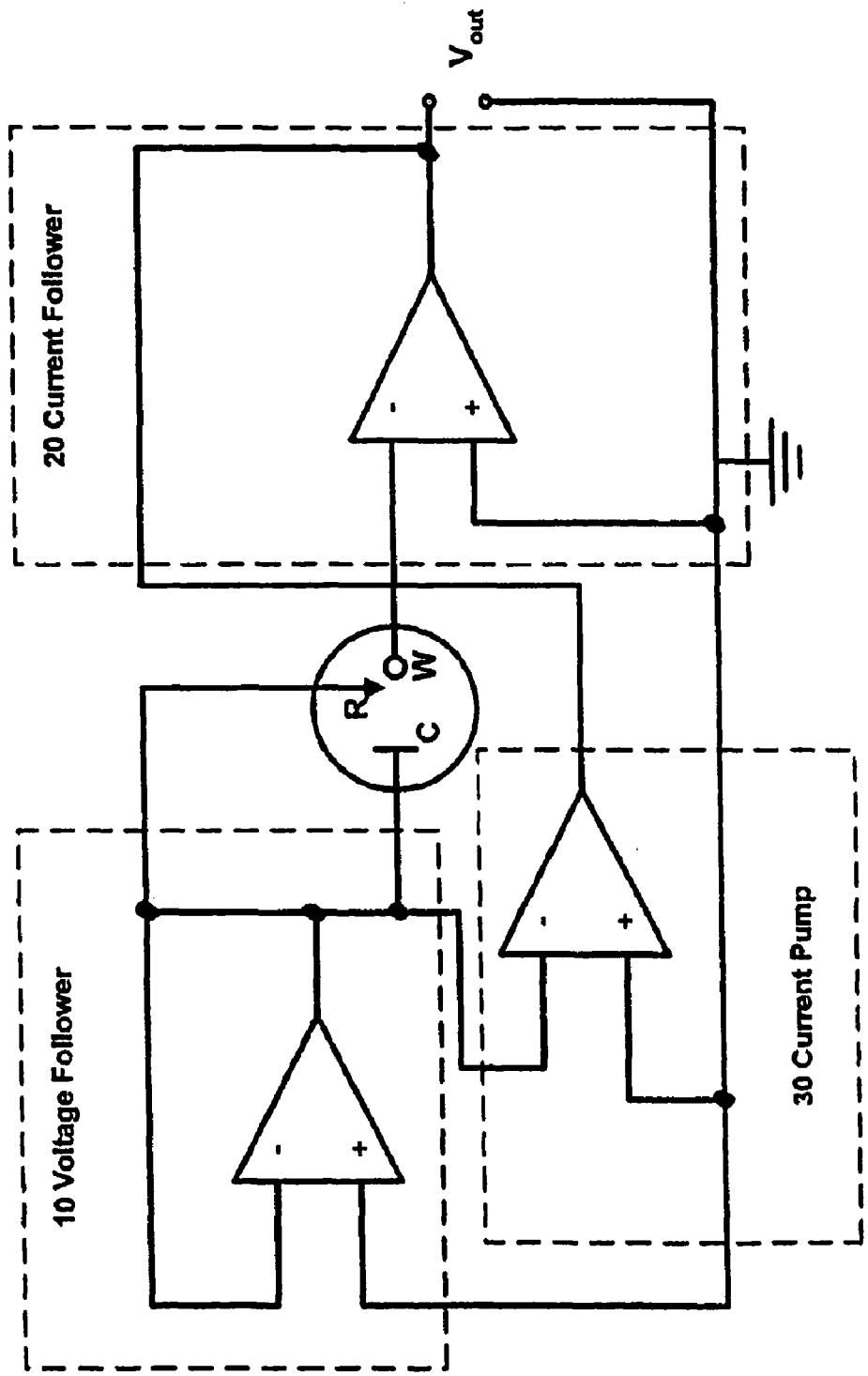
FIG. 13B is a block diagram of one embodiment of the measurement circuitry for use in the present invention.

FIG. 13B shows a block diagram of one embodiment of a measurement circuit of the present invention. In FIG. 13B, the voltage follower (10) and current follower (20) sections function as known to one skilled in the art. See, for example, A. J.

Bard and L. R. Faulkner, *Electrochemical Methods: Fundamentals and Applications*, John Wiley & Sons: New York (1980), the disclosure of which is incorporated herein by reference. The voltage follower maintains a constant potential between the reference electrode (R) and the working electrode (W). The current follower buffers and amplifies currents which flow in the electrochemical sensor between the counter electrode (C) and the working electrode (W). The current pump (30) applies electronic interrogation to the sensor by forcing a known current to flow between the counter electrode (C) and the working electrode (W).

The foregoing description and accompanying drawings set forth preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A method of adjusting the output of an electrochemical sensor including a working electrode and a counter electrode, comprising:
    electronically causing a current flow between the working electrode and the counter electrode via an electrolyte independent of the presence of a test gas;
    measuring a response of the sensor to the current demand resulting from the electronically generated current flow; and
    applying an algorithm comprising a correction factor based upon the measured response to correct the sensor output during sampling of an analyte gas to compensate for changes in sensitivity of the sensor over time.

2. The method of claim 1 wherein a constant current is caused to flow between the working electrode and the counter electrode and the measured response is a potential difference.

3. The method of claim 1 wherein a constant potential difference is maintained between the working electrode and the counter electrode and the measured response is current.

4. The method of claim 1 wherein the electrochemical sensor further comprises a reference electrode.

5. The method of claim 1 wherein the electrolyte is a liquid electrolyte.

6. The method of claim 5 wherein the electrolyte is an aqueous electrolyte or an organic electrolyte.

7. The method of claim 1 wherein the electrolyte is a quasi-solid electrolyte.

8. The method of claim 7 wherein the quasi-solid electrolyte comprises a liquid ionic conductor immobilized by a high-surface-area, high-pore-volume solid.

9. The method of claim 1 wherein the electrolyte is a solid ionic conductor.

10. A sensor comprising:
    a working electrode;
    a counter electrode;
    an electrolyte;
    a power source in electrical connection with the working electrode and the counter electrode to electronically cause a current flow between the working electrode and the counter electrode of the presence of a test gas;
    circuitry to measure a response of the sensor to the electronically generated current flow; and
    an output system which corrects the output of the sensor during sampling of an analyte gas as a function of the measured response of the sensor to the electronically generated current flow to compensate for changes in sensitivity of the sensor over time.

11. The sensor of claim 10 wherein a constant current is caused to flow between the working electrode and the counter electrode and the measured response is a potential difference.

12. The sensor of claim 10 wherein a constant potential difference is maintained across the working electrode and the counter electrode and the measured response is current.

13. The sensor of claim 10 wherein the electrochemical sensor further comprises a reference electrode.

14. The sensor of claim 10 wherein the electrolyte is a liquid electrolyte.

15. The sensor of claim 14 wherein the electrolyte is an aqueous electrolyte or an organic electrolyte.

16. The sensor of claim 10 wherein the electrolyte is a quasi-solid electrolyte.

17. The sensor of claim 16 wherein the quasi-solid electrolyte comprises a liquid ionic conductor immobilized by a high-surface-area, high-pore-volume solid.

18. The sensor of claim 10 wherein the electrolyte is a solid ionic conductor.

19. The sensor of claim 10 wherein the output system includes an adjustment algorithm to correct the output of the sensor.

* * * * *

UNITED STATES PATENT AND TRADEMARK OFFICE
CERTIFICATE OF CORRECTION

| | | |
|---|---|---|
| PATENT NO. | : 7,959,777 B2 | Page 1 of 1 |
| APPLICATION NO. | : 12/215295 | |
| DATED | : June 14, 2011 | |
| INVENTOR(S) | : Towner B. Scheffler | |

It is certified that error appears in the above-identified patent and that said Letters Patent is hereby corrected as shown below:

In column 10, line 15, claim 10, insert the word -- independent -- after the word electrode.

Signed and Sealed this
Fourteenth Day of February, 2012

David J. Kappos
*Director of the United States Patent and Trademark Office*